(12) United States Patent
Shtul

(10) Patent No.: US 9,072,469 B2
(45) Date of Patent: Jul. 7, 2015

(54) ENDOSCOPIC DEVICE INSERTABLE INTO A BODY CAVITY AND MOVABLE IN A PREDETERMINED DIRECTION, AND METHOD OF MOVING THE ENDOSCOPIC DEVICE IN THE BODY CAVITY

(75) Inventor: Boris Shtul, Haifa (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 783 days.

(21) Appl. No.: 11/982,059

(22) Filed: Nov. 1, 2007

(65) Prior Publication Data

US 2009/0264704 A1    Oct. 22, 2009

Related U.S. Application Data

(60) Provisional application No. 60/855,959, filed on Nov. 1, 2006.

(51) Int. Cl.
| | | |
|---|---|---|
| A61M 31/00 | (2006.01) | |
| A61M 37/00 | (2006.01) | |
| A61B 1/00 | (2006.01) | |
| A61B 1/04 | (2006.01) | |
| G01N 21/00 | (2006.01) | |
| A61B 1/12 | (2006.01) | |
| A61B 1/005 | (2006.01) | |

(52) U.S. Cl.
CPC ............. *A61B 1/126* (2013.01); *A61B 1/00094* (2013.01); *A61B 1/00156* (2013.01); *A61B 1/005* (2013.01); *A61B 1/0014* (2013.01); *A61B 1/00147* (2013.01)

(58) Field of Classification Search
USPC ......... 600/104, 106, 114–116, 129, 156, 127, 600/219, 139–152; 604/95.01–95.05, 264, 604/271; 356/241.1–241.6
See application file for complete search history.

(56) References Cited

U.S. PATENT DOCUMENTS

| | | | | |
|---|---|---|---|---|
| 2,704,541 | A | * | 3/1955 | Wyatt .............................. 600/184 |
| 2,767,705 | A | * | 10/1956 | Moore .......................... 600/184 |
| 4,176,662 | A | * | 12/1979 | Frazer ............................ 600/114 |
| 5,398,670 | A | * | 3/1995 | Ortiz et al. ..................... 600/114 |
| 5,595,565 | A | | 1/1997 | Treat et al. |
| 5,906,591 | A | * | 5/1999 | Dario et al. ................. 604/95.03 |
| 6,517,477 | B1 | * | 2/2003 | Wendlandt .................... 600/114 |
| 6,702,734 | B2 | | 3/2004 | Kim et al. |
| 6,911,004 | B2 | | 6/2005 | Kim et al. |
| 6,939,291 | B2 | * | 9/2005 | Phee Soo Jay et al. ........ 600/114 |
| 7,097,612 | B2 | * | 8/2006 | Bertolero et al. ............... 600/37 |

(Continued)

FOREIGN PATENT DOCUMENTS

| | | | | |
|---|---|---|---|---|
| WO | WO 99/53827 | * | 10/1999 | ............. A61B 1/005 |
| WO | WO 01/54565 | | 8/2001 | |

(Continued)

OTHER PUBLICATIONS

Official Action Dated Mar. 30, 2011 From the US Patent and Trademark Office Re. U.S. Appl. No. 11/975,534.

(Continued)

*Primary Examiner* — Ryan Henderson

(57) ABSTRACT

In an endoscopic device insertable into a body cavity attachable elements are moved over one another to move forwardly of each other and to leave each other behind, and to move along different paths so as not to be attached to the same areas of a wall of the body cavity.

14 Claims, 8 Drawing Sheets

(56) References Cited

U.S. PATENT DOCUMENTS

| | | | |
|---|---|---|---|
| 7,699,771 B2* | 4/2010 | Wendlandt | 600/115 |
| 7,909,755 B2* | 3/2011 | Itoi | 600/153 |
| 2005/0080438 A1 | 4/2005 | Weller et al. | |
| 2005/0177069 A1 | 8/2005 | Takizawa et al. | |
| 2008/0064930 A1* | 3/2008 | Turliuc | 600/156 |
| 2008/0103360 A1 | 5/2008 | Shtul | |
| 2010/0016663 A1* | 1/2010 | Maisch et al. | 600/114 |
| 2012/0078047 A1 | 3/2012 | Shtul | |
| 2013/0317292 A1 | 11/2013 | Shtul | |

FOREIGN PATENT DOCUMENTS

| | | |
|---|---|---|
| WO | WO 03/013348 | 2/2003 |
| WO | WO 2009/010828 | 1/2009 |

OTHER PUBLICATIONS

Notification of Publication of Patent Application for Invention and Entering Into the Substantive Examination Procedure Dated May 11, 2011 From the Patent Office of the State Intellectual Property Office of the People's Republic of China Re. Application No. 200780043762.8 and Its Translation Into English.
Translation of Notification of Office Action Dated Dec. 19, 2012 From the State Intellectual Property Office of the People's Republic of China Re. Application No. 200780043762.8.
Restriction Official Action Dated Nov. 14, 2012 From the US Patent and Trademark Office Re. U.S. Appl. No. 13/245,976.
International Search Report and the Written Opinion Dated Dec. 7, 2012 From the International Searching Authority Re. Application No. PCT/IB2007/004611.
International Preliminary Report on Patentability Dated Dec. 28, 2012 From the International Bureau of WIPO Re. Application No. PCT/IB2007/004611.
Communication Pursuant to Rules 70(2) and 70a(2) EPC Dated Jan. 9, 2014 From the European Patent Office Re. Application No. 07875154.2.
Supplementary European Search Report and the European Search Opinion Dated Dec. 13, 2013 From the European Patent Office Re. Application No. 07875154.2.

* cited by examiner

ENDOSCOPIC DEVICE INSERTABLE INTO A BODY CAVITY AND MOVABLE IN A PREDETERMINED DIRECTION, AND METHOD OF MOVING THE ENDOSCOPIC DEVICE IN THE BODY CAVITY

CROSS-REFERENCE TO A RELATED APPLICATION

This application claims priority from provisional application Ser. No. 60/855,959 filed on Nov. 1, 2006.

BACKGROUND OF THE INVENTION

The present invention relates to devices for endoscopic examination which are movable in a body cavity in a predetermined direction without pushing from outside, for example in intestine and can carry equipment that are necessary for diagnostics and treatment of the intestine. It also relates to a method of moving such devices in a body cavity.

There are many devices of this type; however they are not used in practice. Medical personnel move medical instruments and diagnostic equipment into intestine manually. Taking into consideration that the intestine has a complicated shape and length about 1.5 meter it is quite a difficult problem for the medical personnel. During this process, the intestine is subjected to significant deformations which cause pain to a patient and sometimes perforations of an intestine wall. The above mentioned deformations are caused, because along the whole length of the intestine the direction of a force which moves the device and the direction of its movement do not coincide with one another.

The devices disclosed in the patents are designed to solve this problem, so that the devices are moved in a self-moving manner and carry the equipment which is necessary for diagnostics and treatment. When the device is introduced into an intestine, it moves further under the action of a force applied to its front part relative to the wall of the intestine and directed along the intestine. The movement is carried out by small steps, and within each of the steps the direction of movement coincides with the direction of the applied force. As a result, the deformations of the intestine should be minimal. However, in order to apply the force relative to the wall of the intestine, it is necessary to provide a point of support. This poses the major problem since the walls of the intestine are very slippery, thin and elastic in a transverse direction. In the known devices the corresponding elements formed as legs, prongs, balloons, etc., still cause deformation of the intestine from inside when these elements try to engage the walls of the intestine.

U.S. Pat. No. 5,906,591 to Dario, et al discloses an endoscopic robot which, for its movement, provides points of support by means of vacuum attaching elements formed as two perforated cylinders located one behind the other. The attaching elements formed in this way are not efficient, since the openings in them are very small. In addition they are arranged over the whole surface of the cylinders, so that generation of a vacuum is not guaranteed. It suffices to have one opening which does not touch the wall of the intestine, and the vacuum in the corresponding attaching element disappears. If level of vacuum is increased in order to improve efficiency, the walls of the intestine can be damaged. Also, the negative factor from the point of view of safety of intestine walls is that during the movement the attaching elements formed in this way pass the same point twice, by the front attaching element and then by the rear attaching element. Also, it is difficult to connect additional diagnostic or treatment elements to the device disclosed in this reference.

Another device of this type—is disclosed for example in a U.S. published patent application. This application discloses a device in which there are two attaching elements which are aligned with one another and are displaced by small steps consecutively one after the other over the same path in a longitudinal direction and alternatingly attached to a wall of the intestine under the action of vacuum and pressure. While this device can be considered an improvement, the disadvantage of this device is the particular trajectory of movement, in accordance with which the two attaching elements move one after the other over the same line. When one of the attaching elements is detached from the wall of the intestine the intestine is immediately deformed back, which causes the corresponding problems. It is believed that the existing devices can be further improved.

SUMMARY OF THE INVENTION

Accordingly, it is an object of the present invention to provide an endoscopic device insertable into a body cavity and movable in a predetermined direction, which avoids the disadvantages of the prior art.

In keeping with these objects and with others which will become apparent hereinafter, one feature of the present invention resides, briefly stated, in an endoscopic device insertable into a body cavity movable in a predetermined direction, comprising a housing having an axis extending in a direction substantially corresponding to a direction of movement of the device; movable attaching means which is movable relative to said housing and is attachable to a wall of the body cavity under the action of vacuum in an interior of said movable attaching means and detachable from the wall of the cavity under the action of pressure provided in the interior of said movable attaching means; and immovable attaching means which is immovably connected with said housing and is attachable to a wall of the body cavity under the action of vacuum in an interior of said immovable attaching means and detachable from the wall of the cavity under the action of pressure provided in the interior of said immovable attaching means, said immovable attaching means and said movable attaching means being alternatingly attachable to the wall of the cavity; so that when said movable attaching means is attached to the wall of the cavity and said immovable attaching means is not attachched to the wall of the cavity, said housing can be displaced in the direction of movement, while when said immovable attaching means is attached to the wall of the cavity, said movable attaching means can be displaced in a longitudinal direction without displacement of said housing, said movable attaching means and immovable attaching means being arranged so that they are attachable to different locations on the wall of the intestine as considered in a direction transverse to said axis of said housing.

When the device is designed in accordance with the present invention, it is configured as a simple, inexpensive, safe and reliable device for moving without pushing from outside along the whole length of intestine, while carrying an equipment which is necessary for a doctor for diagnostics and treatment of sicknesses of the intestine, for example a video camera, surgical instruments, etc.

The device is beneficial for the patient, since the process of movement along the intestine is not accompanied by significant deformation of the intestine and therefore does not cause pain. A significant surface of the attaching elements which contact with the walls of the intestine allows to obtain a reliable attachment with low level of vacuum. The presence of special grates additionally increases the attachment with the intestine and makes possible a further reduction of vacuum.

The device has the system which prevents accumulation of mucus in the attaching elements and pipes which lead to them, and guarantees the reliable operation of the device during the whole procedure.

The exceptionally important feature is that when the device moves in one direction, the attaching means are never attached to the same point of the intestine.

The unique feature of the new device is the automatic adaptation to transverse size of the intestine. The situation is optimal when the transverse size of the device is somewhat smaller or equal to the transverse size of the intestine. It is very important from the point of view of ability of the device to move along the intestine, and at the same time from the point of safety since it reduces pressure on its walls. The majority of healthy people have a diameter or intestine between 20 mm and 60 mm. However, different portions or intestine can have different diameters. In sick people these differences are increased.

The transverse size of the device is determined by a maximum distance between the lateral attaching elements which are located at both sides of the housing. The connection with the housing is carded out so that this lateral immovable attaching elements are immovable relative to the longitudinal axis of the device but they have two degrees of freedom relative to a transverse axis. After the device is introduced into the intestine, the lateral immovable attaching elements are spread to contact the walls of the intestine. This is performed under the action of a small force created by elastic pipes which are connected to the attaching elements. The magnitude of force which spreads the immovable attaching elements is selected so that they just touch the walls of the intestine and do not deform them. Therefore, in the process of movement of the device the lateral immovable attaching elements slide along the intestine, and the distance between them is determined directly by a transverse size of the intestine itself.

The device also satisfies the needs of doctors because it is exceptionally simple and low cost device. The device is composed of several plastic parts which have low manufacturing costs, so that the device can be made as a disposable device and does not need any sterilization. The device also satisfies the requirements of manufactures, since it has a low cost and therefore can be priced with a low price for buyers thus increasing the market.

An additional important advantage of the device is a low degree of integration of the device with the instruments attached to it. Presently, the instruments used by doctors are designed so that they pass through an operation passage located inside a colonoscopic device and having its integral part. It applies significant demands to the instruments. The concept of an open device in accordance with the present invention removes these limitations and opens new possibilities for the manufactures of the instruments.

In accordance with another feature of the present invention an endoscopic device insertable into a body cavity movable in a predetermined direction has a housing having an axis extending in a direction substantially corresponding to a direction of movement of the device; first attaching means which is attachable to a wall of the body cavity under the action of first in an interior of said movable attaching means and detachable from the wall of the cavity under the action of pressure provided in the interior of said first attaching means; second attaching means which is attachable to a wall of the body cavity under the action of vacuum in an interior of said second attaching means and detachable from the wall of the cavity under the action of pressure provided in the interior of said second attaching means, said first attaching means and said second attaching means being alternatingly attachable to the wall of the cavity; so that and means for alternating attaching said first attaching means and said second attaching means to the wall of the cavity one of said attaching means is attached to the wall of the cavity, then the other of said attaching means is moved forwardly of said one attaching means behind, then the one of said attaching means is moved forwardly of said other attaching means behind, et.

In accordance with a further feature of the present invention a method of inserting an endoscopic device into a body cavity and moving in a predetermined direction, comprising the steps of providing a housing having an axis extending in a direction substantially corresponding to a direction of movement of the device; providing first attaching means which is movable relative to said housing and is attachable to a wall of the body cavity under the action of vacuum in an interior of said first attaching means and detachable from the wall of the cavity under the action of pressure provided in the interior of said first attaching means; providing second attaching means which is attachable to a wall of the body cavity under the action of vacuum in an interior of said second attaching means and detachable from the wall of the cavity under the action of pressure provided in the interior of said second attaching means; alternating attaching said first attaching means and said second attaching means to the wall of the cavity by attaching one of said attaching means to the wall of the cavity, then moving the other of said attaching means forwardly of said one attaching means to leave said one attaching means, behind, then moving said one attaching means forwardly of said other attaching means to leave said other attaching means behind, etc.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1A:
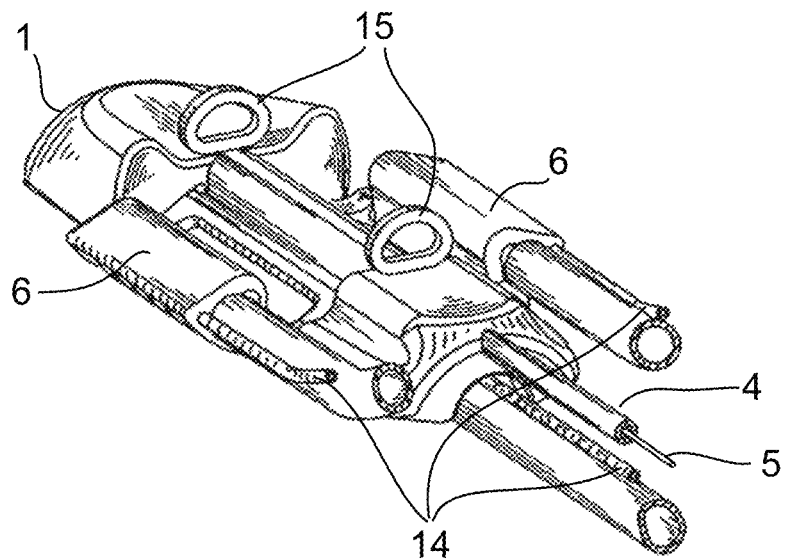
FIG. 1a is a perspective view of an endoscopic device insertable into a body cavity and movable in a predetermined direction as seen from below in accordance with the present invention.

The endoscopic device in accordance with the present invention, which is insertable into a body cavity and movable in a predetermined direction has a housing which is identified with reference numeral 1. The housing is substantially elongated in a direction of a longitudinal axis and does not have any sharp edges to prevent damages to a wall of a body cavity, such as an intestine. The housing 1 in its interior has an omega-shaped slot 2, shown in FIGS. 1 and 3 that extends in a longitudinal direction.

The device in accordance with the present invention has a movable attaching element which is identified with reference numeral 3. The movable attaching element 3 is movable relative to the housing 1 and guided by the slot 2. In particular, a projection of the movable attaching element 3 engages in the slot 2 provided in the housing.

A force required for movement of the movable attaching element 3 relative to the housing 1 and relative to a wall of the body cavity, for example intestine, is generated by a power aggregate which can be located in a control block, and is transmitted to the movable attaching element through a transmission. The power aggregate can be formed as any mechanism which performs a reciprocal movement (a pneumatic cylinder-piston unit, an electrical solenoid, etc). the power aggregate can be also located in/on the housing 1.

Figure 1B:
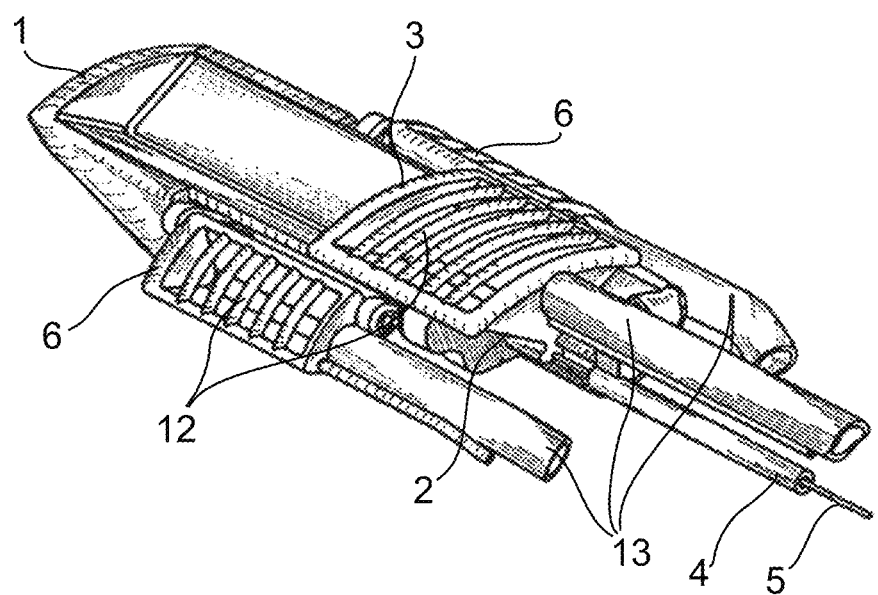
FIG. 1b is a perspective view of an endoscopic device insertable into a body cavity and movable in a predetermined direction in accordance with the present invention as seen from above.

The transmission is formed as a well known mechanism, for example including a thin cable 5 which is located inside a flexible pipe 4. The pipe 4 is connected to the housing 1 and also to a casing of the power aggregate, while the cable 5 is connected with one end to the movable attaching element and with its opposite end to an element of the power aggregate which performs the reciprocating movement. FIG. 1b shows the omega-shaped slot 2 and the point of connection of the cable 5 to the movable attaching element 3.

Figure 4A:
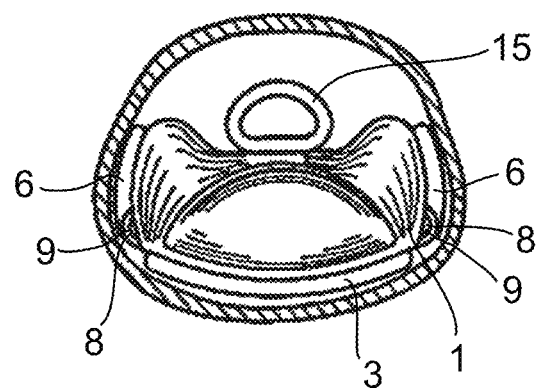
FIGS. 4a and 4b are views showing the endoscopic device in accordance with the present invention insertable into a body cavity and located in an intestine with a smaller diameter and with a larger diameter correspondingly.
Figure 4B:
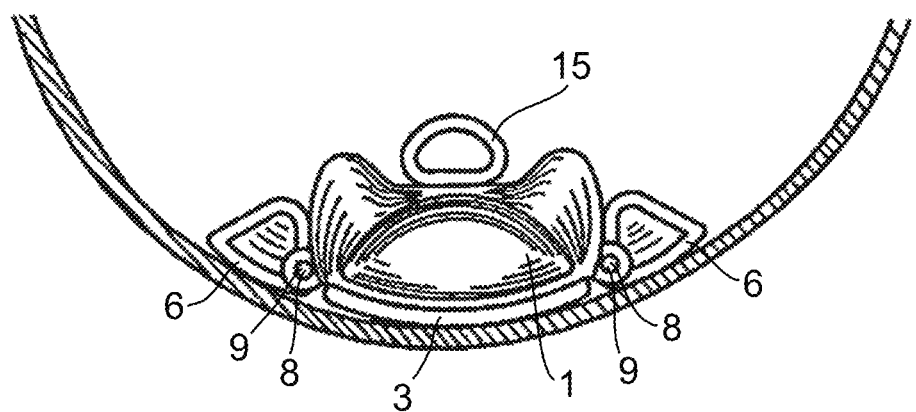

The device further has preferably, two immovable attaching elements which are identified with reference numeral 6. The immovable attaching elements 6 are connected with the housing 1 so that they can not move longitudinally relative to the housing. However, they can turn and somewhat shift in a plane extending perpendicular to the direction of the movement of the housing. As a result, the transverse size of the device adjusts to changes of an inner diameter of the intestine, and their abutment against the walls of the intestine is very efficient, even if the intestine can have different diameters. FIG. 4a shows the position of the immovable attaching elements 6 in an intestine having a diameter 20 mm, while FIG. 4b shows a position of the immovable attaching elements in an intestine having a diameter of 60 mm.

Figure 2A:
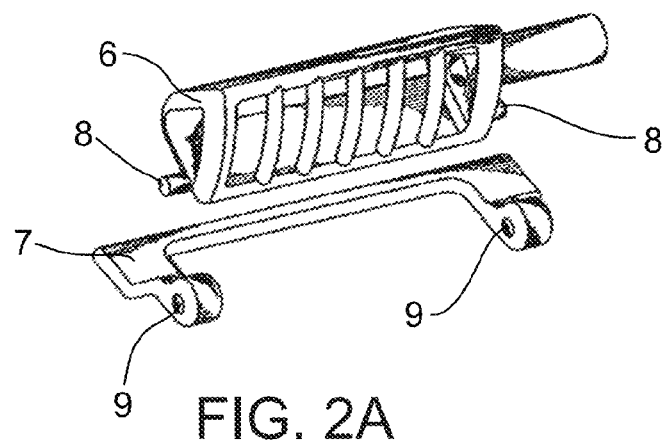
FIGS. 2a and 2b are views showing details of an attaching element of the device in accordance with the present invention.
Figure 2B:
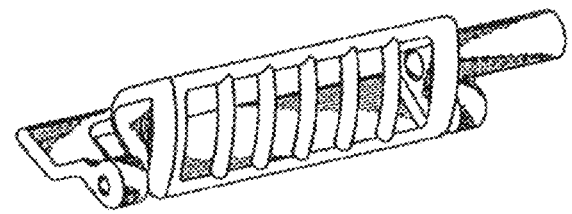
Figure 3:
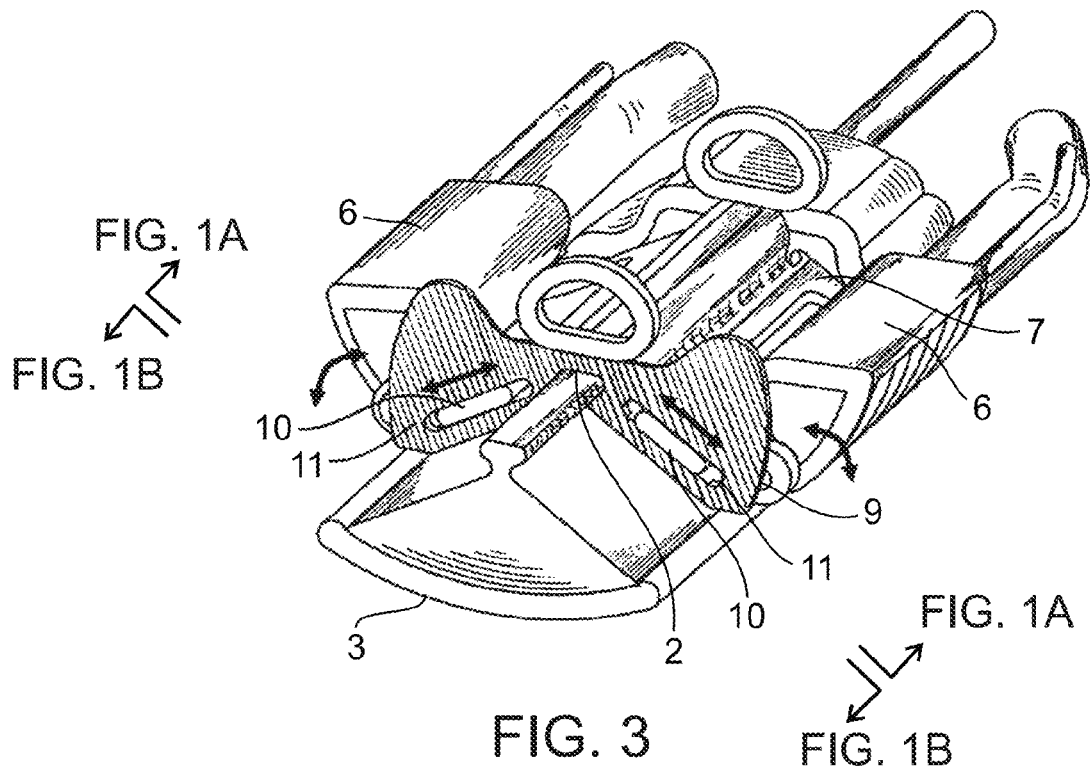
FIG. 3 is a view showing the inventive device with a partially removed front part and showing further details of the device.

FIGS. 2a, 2b and 3 show the connection of the immovable attaching elements 6. First, they are connected to an intermediate plate 7 by cylindrical pins 8 which are inserted into openings of lugs 9 of the intermediate plate. The dimensions of the pins and the openings are selected to allow free turning of the movable attaching elements over a certain angle. The plate 7 is mounted on the housing 1 so that its side projections 10 are inserted into grooves 11 as shown in FIG. 3. On this figure a front part is removed to show the grooves 11, in which the intermediate plate 7 can move in a direction shown by the arrows. The combination of these two degrees of freedom, namely turning and displacement, allows the immovable attaching elements 6, which are immovable in the longitudinal direction relative to the housing, to slide along the wall or intestine and change their position depending on its diameter. The transverse deformation of intestine and the resulting problems are therefore minimal.

Figure 5A:
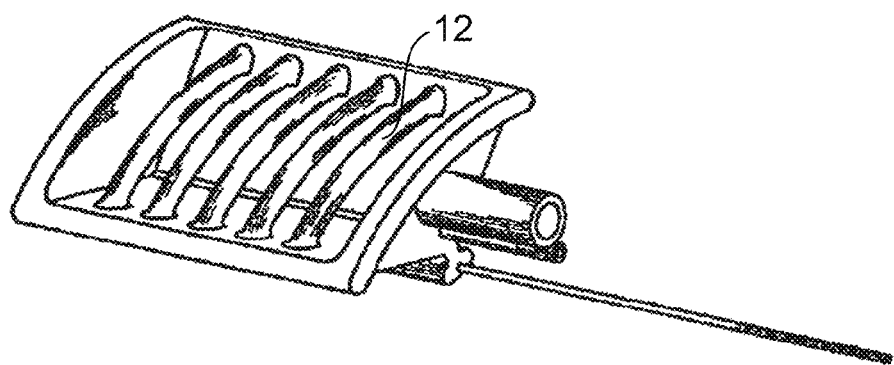
FIGS. 5a, 5b and 5c are view showing several embodiments of the attaching elements.
Figure 5B:
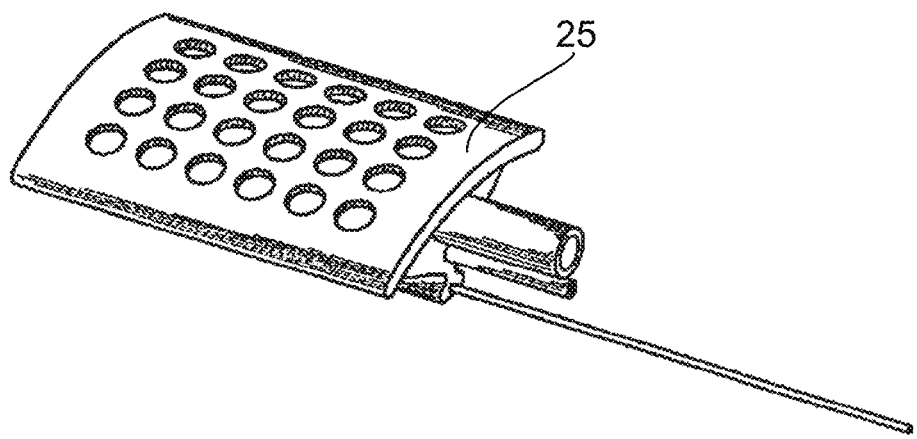
Figure 5C:
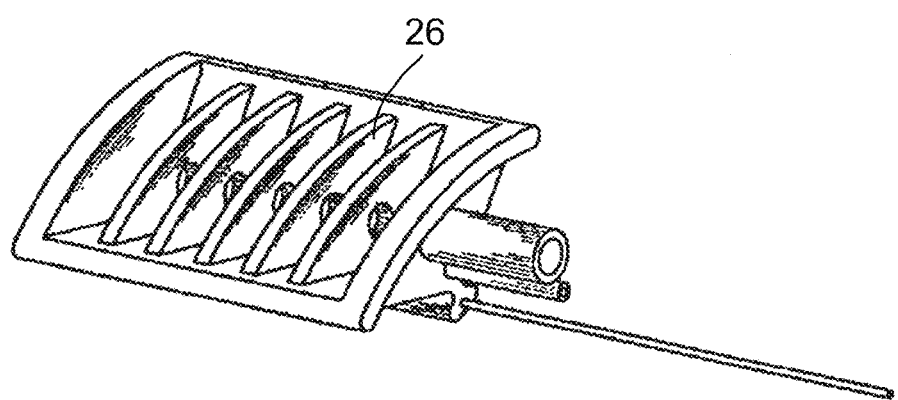

Each of the attaching elements 3 and 6 is formed as a hollow body with an opening provided in its one wall and extending substantially over a whole surface facing the wall of the intestine. The hollow body can be cup-shaped with a convex wall that contains the opening. The opening is provided with an element which prevents sucking of the intestine wall into the interior of the attaching element and at the same time increases adherence with the intestine wall. As shown in FIGS. 1b and 5a this element can be formed as a convex grate 12 which is oriented perpendicular to the direction of movement of the housing and is adapted to be in contact with the intestine wall. It also can be formed as a perforated plate 25 with openings shown in FIG. 5b, or as a ribbed assembly shown in FIG. 5c.

The attaching elements 3 and 6 are connected with the control block by elastic houses 13, through which alternatingly vacuum and pressure are supplied to the attaching elements.

Figure 6:
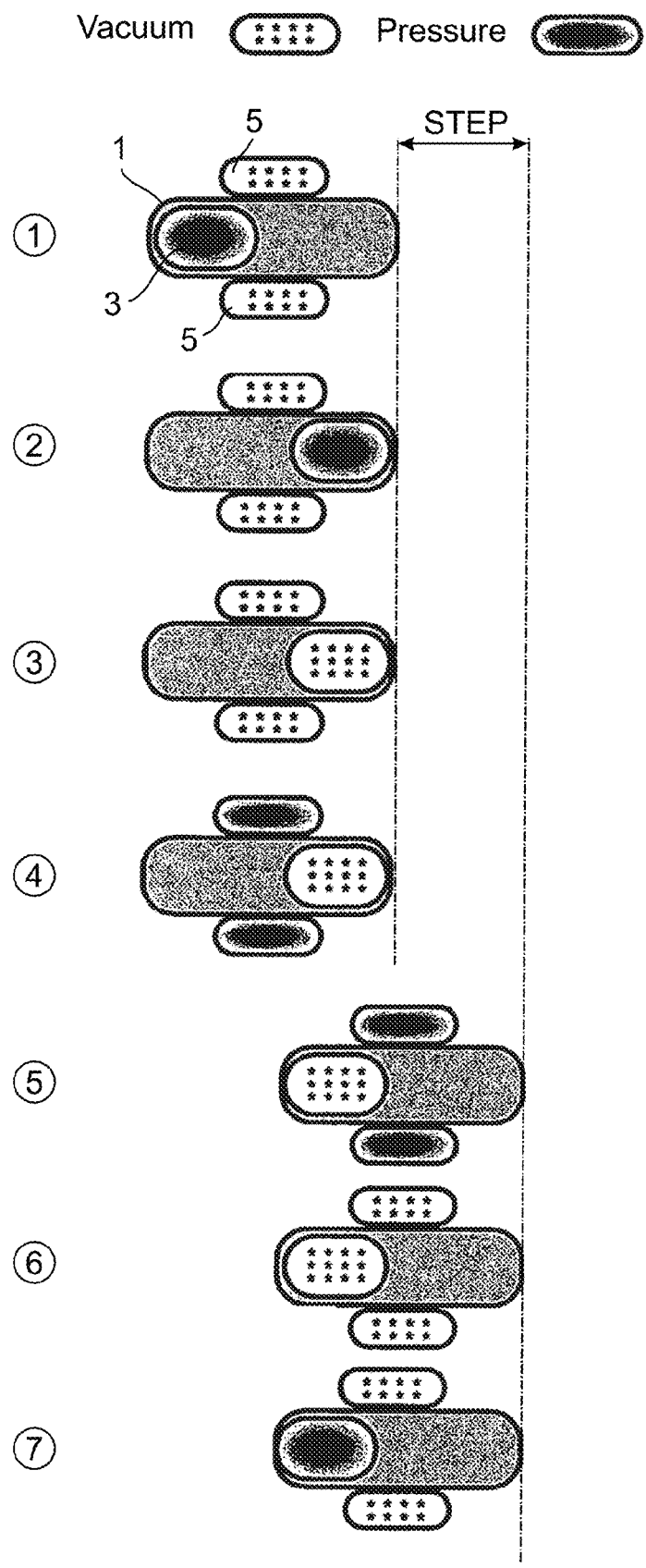
FIG. 6 is a view schematically showing corresponding steps of movement of the endoscopic device in accordance with the present invention insertable into a body cavity and movable in a predetermined direction.

The inventive device operates in the following manner, as schematically shown in FIG. 6, which shows displacement of the device over one cycle.

In step 1 the movable attaching element 3 is located in a rear position as seen in the direction of movement of the device and is supplied with pressure so that it is not attached to the intestine wall, while the immovable attaching elements 6 are provided with vacuum and attached to the intestine wall.

In step 2 the cable 5 of the movable attaching element 3 moves forward and therefore the movable attaching element 3 is moved to its forward position.

In step 3 vacuum is supplied to the movable attaching element 3 and it is attached to the intestine wall, or in other words it is fixed in this position.

In step 4 pressure is supplied to the immovable attaching elements 6 and they are detached from the intestine wall.

In step 5 the cable 5 of the movable attaching element 3 is displaced rearwardly so that the housing 1 is moved forwardly by one step.

In step 6 vacuum is supplied into the immovable attaching elements 6, and they are attached to the intestine wall so as to fix a new position of the device relative to the intestine wall. This represents the end of the cycle.

In step 7 a pressure is supplied into the movable attaching element 3, and the cycle is repeated again.

It is believed to be clear that in accordance with the present invention, first for example the immovable attaching elements 6 are attached to the wall of the intestine, then the movable attaching element 3 is moved forwardly of the immovable attaching element 6 leaving them behind and is attached to the wall, then the immovable attaching elements 6 are moved forwardly of the movable attaching element 3 leaving it behind, etc. This is achieved by the corresponding generating of vacuum and pressure by the corresponding source means. It is believed to be also understood that the movable attaching element 3 which is located substantially coaxially with an axis of the housing 1 of the device, and the immovable attaching elements which are located at both sides of the axis of the housing 1 and laterally spaced from the axis, are attachable to different locations or areas of the wall of the intestine as considered in a direction transversely to the axis, which is very important to avoid traumatizing of the wall of the intestine.

It is possible that the immovable attaching elements are also movable relative to the housing.

The attaching elements can be also displaced automatically continuously, or discontinuously in a stepped manner.

The device therefore moves step by step along the intestine. By changing the order of the steps, the device can move in an opposite direction.

As mentioned herein above, the movement of the device along the intestine is accompanied by a cyclic attachment of the vacuum-type attaching elements to its walls. The walls of intestine are covered with a great quantity of mucus. Under the action of vacuum, in each cycle of attachment a part of mucus is introduced into the attaching elements and then into thin pipes, along which vacuum/pressure is supplied. The mucus can clog the attaching elements and the pipes.

Figure 7:
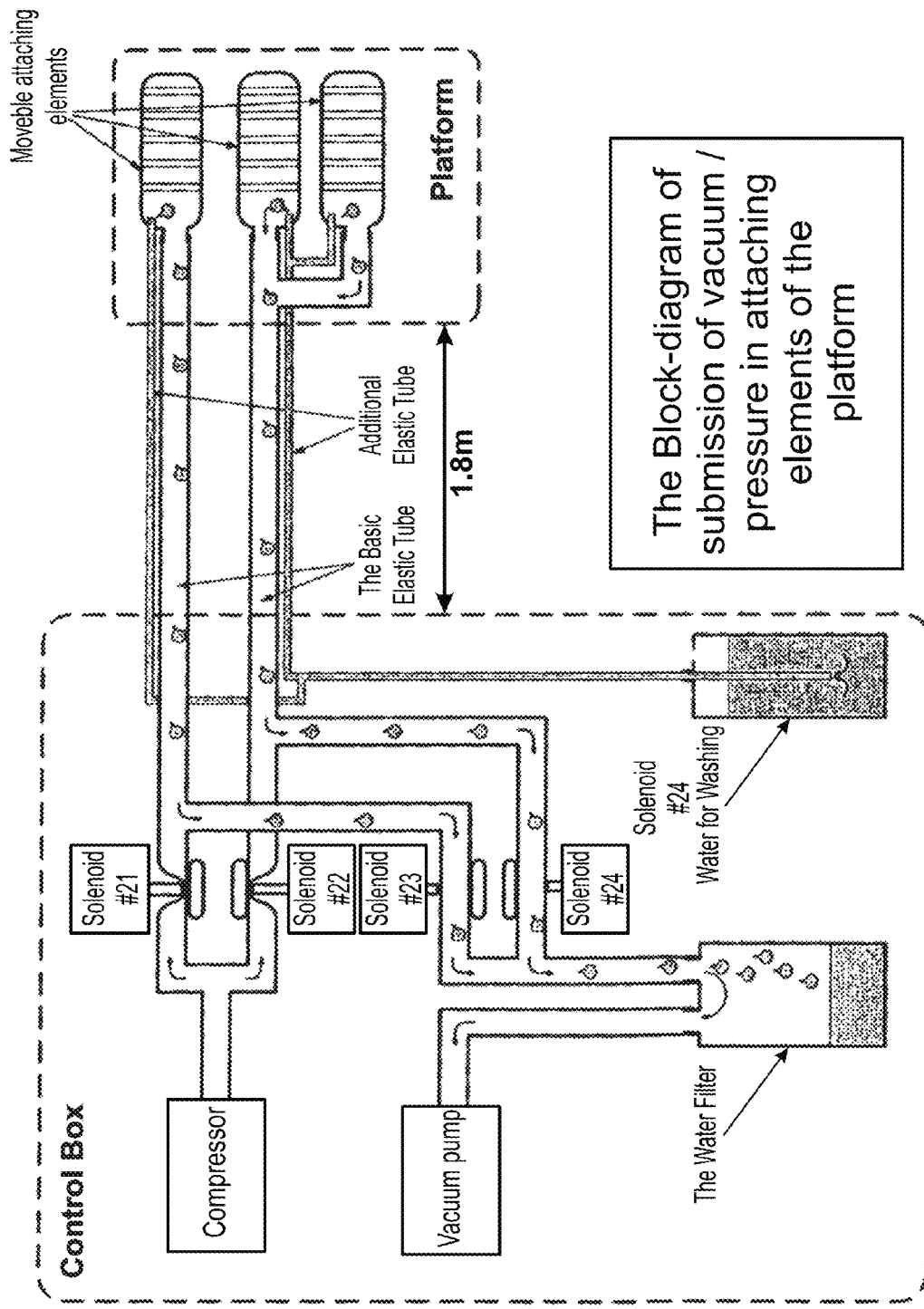
FIG. 7 is a view showing a block-diagram of supply of vacuum/pressure to attaching elements of inventive device.

In order to avoid this, the device in accordance with the present invention is provided with a self-cleaning hydropneumatic system of supply of vacuum/pressure into the attaching elements, which is shown in FIG. 7. This figure does not illustrate additional parts such as monitors, receivers, safety valves, etc., and shows only those elements which are important for the operation of the device.

As explained herein above, the device is moved by means of the attaching elements, in which, in a certain sequence shown in FIG. 6, the vacuum and pressure are supplied. The vacuum and pressure are provided correspondingly by a compressor and a vacuum pump located in a control box and supplied into the attaching elements along elastic pipes or a main elastic tube. FIG. I b shows the pipes identified with reference numeral 13. The pipes extended through valves formed by solenoids 21-24. The location of the pipes relative to the solenoid is selected so that when the solenoid is not supplied with power, its core does not touch the pipe. The solenoid 23 and the solenoid 24 are shown, in this particular condition, and as a result vacuum is supplied to the attaching elements. When power is not supplied to the solenoid, its core is moved out of the housing of the solenoid and squeezes the pipe as shown in the example of the solenoid 21 and 22. It blocks supply of vacuum into the attaching elements.

The control box is provided with an electronic board which is not shown in the drawings and which provides the operation of the solenoids in automatic mode, as well as in manual mode by means of buttons located on the panel of the block.

The prevention of dogging of the attaching elements and elastic pipes with mucus sucked from the walls of the intestine is carried out by introduction into the attachment elements of a washing liquid, in the simplest case-water. Since the movement of the device is accompanied by cyclic alternating operation of vacuum/pressure in the pipes, the liquid located in them performs a reciprocating movement and dissolves mucus which is sucked from the walls of the intestine. By selecting of a corresponding ratio of the vacuum/pressure, in addition to the reciprocating movement it is possible to provide its predominant displacement in a direction from the attaching elements to a vacuum pump. The system also includes a filter which prevents introduction of this liquid into the areas in which the corresponding operation can be disturbed. FIG. 7 shows a system operating in accordance with this principle. Parallel to each of the pipes—the main elastic tube, connected to the attaching elements, an additional elastic tube is introduced. This tube is identified with reference numeral 14 in FIG. 1a. The additional elastic tube can be located both inside the main elastic tube, and also outside the main elastic tube as shown in FIG. 7. The inner diameter of this tube must be 8-10 times smaller than the main elastic tube. One end of each additional tube is introduced into the interior of the attaching element, while the other end is introduced into a vessel located in the control box and filled with water or a special liquid for washing. The water is under atmospheric pressure.

When the system starts operating, then inside the main elastic tube along all its length from the attaching elements to the vacuum pipe, a zone of reduced pressure is generated. As a result, the liquid from the vessel in the control box is aspirated through the additional elastic tube to the place where this tube ends, or in other words into the attaching element and further into the main elastic tube. This is exactly the place where mucus is accumulated.

The influence of supply of this liquid on the operation of the attaching elements connected with the displacement of the device along the intestine is insignificantly low because the additional elastic tube has a very small diameter. Since during the operation of the system, the vacuum and pressure in the attaching element change in a cyclic manner, the liquid performs small reciprocating movements which dilutes mucus. As explained above, with a certain ratio of vacuum/pressure, the mucous will flow in a direction from the attaching elements to the vacuum pump. A water filter is used to prevent entry of the liquid and mucus into the vacuum pump, and this water filter removes liquid and mucous from the system.

The water filter is formed as a vertically located hermetically closed container with two pipes in its upper part. One pipe is connected with the attaching elements from which air and diluted mucus are sucked, while the other pipe is connected with the vacuum pump. Under the action of the vacuum pump, air is sucked from one pipe to the other, while liquid and mucus are moved downwardly under the action of force of gravity. The direction of movement of air and liquid are shown by arrows.

Figure 8A:
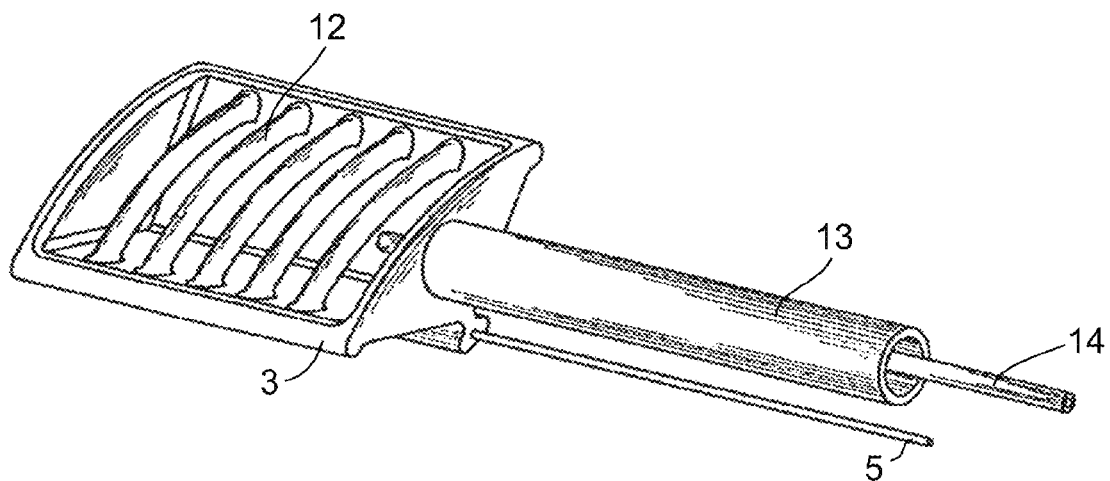
FIGS. 8a and 8b are views showing further embodiments of the attaching elements.
Figure 8B:
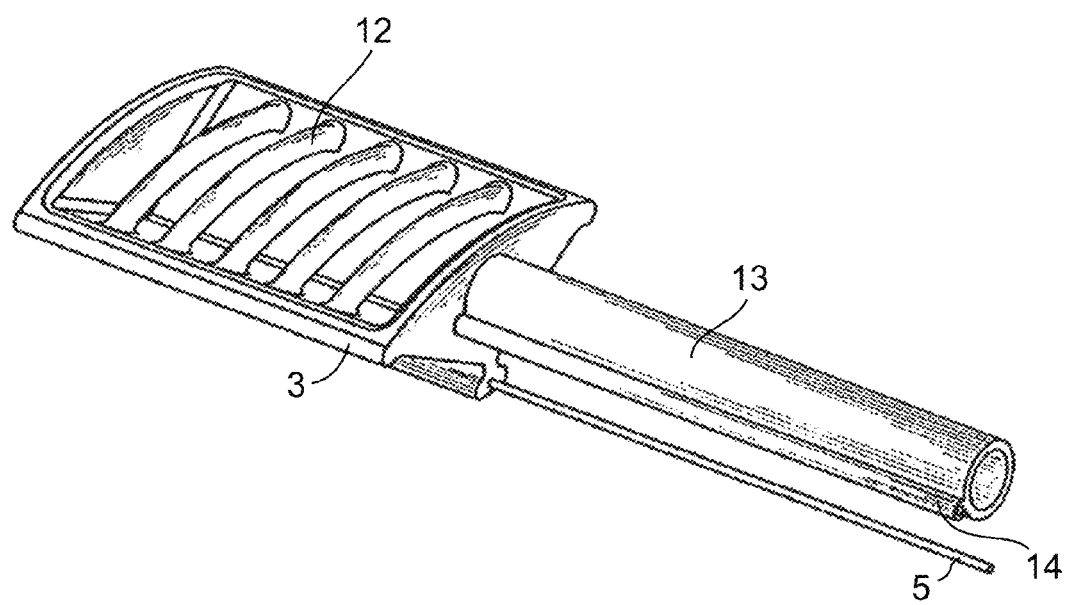

The additional elastic tube can be also located inside the main elastic tube as shown in FIG. 8a, or it can be an integral part of the main tube as shown in FIG. 8b.

Figure 9:
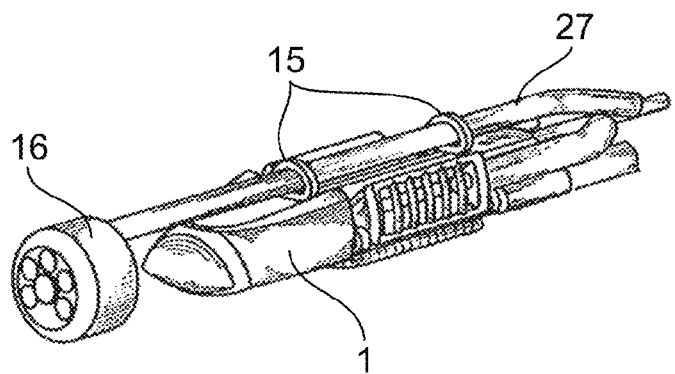
FIGS. 9 and 10 are views showing an endoscopic device in accordance with the present invention with an additional equipment.

As explained herein above, the device carries standard video equipment and operation instruments which are used in gastroenterology. These elements must be connected with the device. FIG. 9 shows the device with the head 16 of a videocamera, which is formed as a separate structural element. It is fixed to the housing 1 of the device by two elastic rings 15, which hold the cable 27 that connects the head with the videocamera located in the control block.

Figure 10:
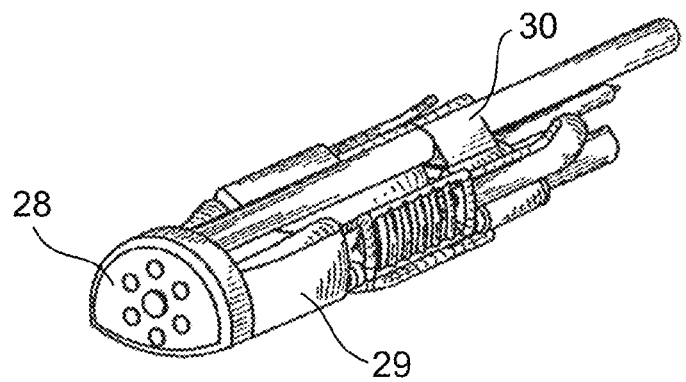
Figure 11:
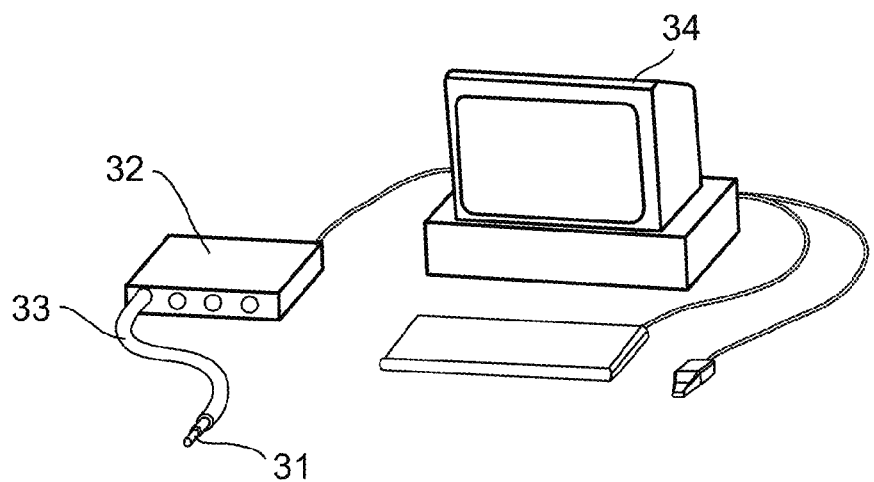
FIG. 11 is a view showing a control equipment for the inventive endoscopic device.

The head of the videocamera can be formed integrally with the device as shown in FIG. 10. The head 28 of the of the videocamera is located in the front part 29 of the housing of the device and make one-piece with it. In this embodiment the cable which connects the head with the videocamera has a permanent connection 30 with the housing of the device. The system for visual diagnostics of intestine with the use of the device is shown in FIG. 11. The system includes a plug 31 for connection to the device.

A control block 32, a long elastic hose 33 and a personal computer 34. The control block contains a pneumatic equipment which allows the displacement of the device inside the intestine. The videocamera is located in the same area, and its output is connected to the personal computer. The device is connected with the control block by a hose with the length of substantially 2 m which allows it to completely investigate the whole intestine. The hose incorporates all communicates between the device and the control block: the pipes, the transmission, the cable for the head of the videocamera, etc.

The device can be composed of materials allowing it to be disposable. It can be formed as a modular device assembled of individual elements, or as a one-piece integral device. Also, several devices can be connected with one another in succession.

It will be understood that each of the elements described above, or two or more together, may also find a useful application in other types of constructions differing from the type described above, for example, each of the attachment elements may be part of a construction having more than two lateral attachment elements.

While the invention has been illustrated and described as embodied in an endoscopic device insertable into a body cavity movable in a predetermined direction, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A device for moving equipment inside an intestine comprising:
   (a) a housing, said housing elongated along a longitudinal axis;
   (b) at least two first attachment elements, each of the two first attachment elements:
      laterally spaced from said longitudinal axis along said housing,
      matingly engaging a slot formed in the housing,
      slidable along the slot in a direction perpendicular to the longitudinal
      rotatable about an axis parallel to the longitudinal axis, and
      immovable relative to the housing along the longitudinal axis;
   (c) a second attachment element located substantially coaxially with said longitudinal axis of said housing, and advanceable along a track formed along the housing;
      said second attachment element configured to be displaced along said longitudinal axis: to a first state in a position distal to said first attachment elements and to a second state in a position proximal to said first attachment elements; and
   (d) a vacuum source coupled to each of the first attachment elements and the second attachment element, and capable of generating a vacuum level to attach the first attachment elements and the second attachment element to a wall of said intestine.

2. The device according to claim 1, wherein said second attachment element can be displaced in a longitudinal direction without displacement of said housing.

3. The device according to claim 1, wherein said first attachment elements are moveable in a plane extending perpendicular to said longitudinal axis of said housing to adjust to changes of an inner diameter of said intestine.

4. The device according to claim 3, wherein said movement comprises a turn and a shift.

5. The device according to claim 1, wherein said device comprises at least one coupling element to couple said housing to external equipment for at least one of diagnosis and treatment of said intestine, such that movement of said device through said intestine carries said external equipment inside said intestine.

6. The device according to claim 1, further comprising grates, said grates coupled to said first attachment elements and said second attachment element, said grates configured to prevent sucking of said wall of said intestine into an interior of said first attachment elements and said second attachment element.

7. The device according to claim 6, wherein said grates are oriented perpendicular to said axis.

8. The device according to claim 1, wherein a transverse size of an expanded state of said device ranges from 20 mm to 60 mm.

9. The device according to claim 1, wherein each of said first attachment elements have two degrees of freedom in a plane extending perpendicular to said axis of said housing.

10. The device according to claim 9, wherein said two degrees of freedom comprises a turn and a shift.

11. A method of moving a device to transport equipment inside an intestine comprising:
   attaching two first attachment elements to a wall of said intestine by applying a vacuum to said first attachment elements, each of the first attachment elements being:
      matingly engaging a slot formed in a housing,
      slideable along the slot in a direction perpendicular to a longitudinal axis of said housing,
      rotatable about an axis parallel to the longitudinal axis of the housing, and
      immovable relative to the housing along the longitudinal axis of the housing;
   detaching a second attachment element from said wall of said intestine by applying a pressure to said second attachment element;
   moving said second attachment element along a track formed along the housing,
   the movement being along a longitudinal axis of said intestine from a position proximal to said first attachment elements to a position distal to said first attachment elements, said movement being sufficiently large to overcome a natural elasticity of said intestine;
   attaching the second attachment element to said wall by applying a vacuum to the second attachment element;
   detaching the first attachment elements from said wall by applying a pressure to said first attachment elements;
   moving the first attachment elements so that the second attachment element is restored to a position proximal to said first attachment elements;
   alternating said attaching, said detaching and said moving of said first attachment elements and said second attachment element to move said device along said intestine.

12. The method according to claim 11, further comprising attaching external equipment to said device.

13. The method according to claim 11, wherein alternating comprises alternating said first attachment elements and said second attachment element such that said first attachment elements and said second attachment element are attachable to different areas on said wall of said intestine relative to a direction transverse to said longitudinal axis.

14. The method according to claim 11, further comprising changing an order of said attaching, said detaching and said moving to move said device in an opposite direction.

* * * * *